United States Patent [19]
Malinowski et al.

[11] Patent Number: 5,520,189
[45] Date of Patent: May 28, 1996

[54] INTRAVASCULAR ULTRASOUND IMAGING GUIDEWIRE

[75] Inventors: Igor Malinowski, Harbor City; Robert Siegel, Venice, both of Calif.

[73] Assignee: Coraje, Inc., San Francisco, Calif.

[21] Appl. No.: 221,261

[22] Filed: Mar. 31, 1994

Related U.S. Application Data

[63] Continuation of Ser. No. 552,430, Jul. 13, 1990, abandoned.

[51] Int. Cl.⁶ .................................. A61B 8/00; A61B 8/12
[52] U.S. Cl. ............................ 128/662.030; 128/662.060
[58] Field of Search ...................... 128/660.03, 662.060; 604/99–103; 606/59

[56] References Cited

U.S. PATENT DOCUMENTS

| | | | |
|---|---|---|---|
| 4,248,090 | 2/1981 | Glenn | 128/663.01 X |
| 4,794,931 | 2/1986 | Yock | 128/662.06 |
| 4,862,893 | 9/1989 | Martinelli | 128/662.03 |
| 4,951,677 | 8/1990 | Crowley et al. | 128/662.06 |
| 5,081,993 | 1/1992 | Kitney et al. | 128/662.06 X |
| 5,095,911 | 3/1992 | Pomeronz | 128/662.06 |

OTHER PUBLICATIONS

Roelsedt, Ben; Gusseuhoven "Intravasular, real-time, two dimensional echo cardiography" International Journal of Cardiac Imaging.

*Primary Examiner*—Francis Jaworski
*Attorney, Agent, or Firm*—Walter A. Hackler

[57] ABSTRACT

An ultrasonic imaging guidewire apparatus for ultrasonic diagnostic imaging of blood vessels, comprising: an elongated, flexible, catheter guide (10) having a plurality of electrical conductors, a transducer seat (11), attached to transducer seat (11) an ultrasonic transducer (14), a flexible distal guidewire (12). Distal guidewire (12) may be ended at its distal end with a protective ball (23). A rotary drive unit (28) for rotation of imaging guidewire together with transducer (14), and an electronic computer (30) for processing signals, obtained by reflecting ultrasonic pulses from tissue of the vessel surrounding transducer (14), into cross-sectional images of vessels.

20 Claims, 3 Drawing Sheets

INTRAVASCULAR ULTRASOUND IMAGING GUIDEWIRE

This is a continuation of application Ser. No. 07/552,430 filed on Jul. 13, 1990, now abandoned.

BACKGROUND OF INVENTION

This invention relates to guidewires and catheters used for angioplasty and atherectomy, and devices for intraluminal, ultrasound imaging.

Description of prior art

U.S. Pat. No. 4,794,931 issued to Yock on Jan. 3, 1989 cites a catheter apparatus, system and method of two-dimensional intraluminal ultrasonography combined with a rotating, cutting tool for atherectomy.

The invention described in this patent cites a catheter for atherectomy having an ultrasonic transducer, mounted on rotating atherectomy cutting tool.

The catheter presented in above the patent, although allowing for radial scanning, does not have the ability to view forward, beyond the distal tip of the catheter.

The rotating cutting tool to which the transducer is attached may subject to cutting forces as the tool cuts into a plaque in a stenosed vessel. Such cutting forces may deflect the tool and the transducer, which are attached to a flexible drive cable. This creates a potential for instability of the axis of rotation of the scanning element and thus affect the stability and quality of the image.

The catheter quoted in the referenced article has a rotating mirror element, which reflects an ultrasound beam from a stationary transducer, deflecting said beam into a direction perpendicular to the axis of the catheter.

This creates the potential for unstable geometry of the ultrasound beam deflection and collection system, and thus for producing an image of poor quality and consistency.

The above mentioned inventions present an interesting embodiment of catheters for intraluminal ultrasound imaging, but nevertheless suffer from a number of disadvantages, such as:

Large size and poor flexibility and thus an inability to access coronary vessels, and to scan in narrowly occluded areas of blood vessels.

Inability to effectively combine the ultrasound imaging and general angioplasty catheter.

Inability to assess the vessel diameter and choose the catheter size, without inserting imaging catheters.

Necessity to insert a catheter for ultrasound imaging and then a second catheter for angioplasty, which means repeated trauma to the blood vessel.

Inability to center catheter in the vessel if the vessel is larger than the outside diameter of the catheter sheath.

BRIEF SUMMARY OF THE PRESENT INVENTION

The present invention describes an apparatus consisting of a special guidewire, equipped with an ultrasonic transducer, a drive unit, for rotation of guidewire and an electronic computer. The guidewire may be located in a central lumen of an angioplasty catheter.

The electronic computer receives and processes signals from the ultrasonic transducer, mounted on the guidewire, as well as transforms signals received into a video image having diagnostic value to the physician.

The transducer element is attached to an enlarged and flattened part of the guidewire, located near the distal end of guidewire.

When an angioplasty catheter is placed in a vessel over the imaging guidewire, the transducer is located distally in front of a balloon angioplasty catheter. The balloon may be inflated with light pressure to center the angioplasty catheter and imaging guidewire in the vessel, for better imaging.

Objects and Advantages

Accordingly besides the objects and advantages of the present invention described above in my patent application, several objects and advantages of the present invention are:

(a) Having a small diameter and therefore the ability to enter coronary vessels and perform ultrasonic scans in the narrowly occluded areas.

(a) Having the ability to inspect occluded areas of blood vessels, prior to insertion of the angioplasty catheter, thus providing information useful in selection of the catheter size.

(c) Having no need for insertion of a special imaging catheter, prior to angioplasty, and thus reduction in patient trauma, and chances of damage to vessel walls.

(d) Having a simple and inexpensive construction of imaging guidewire.

(f) Conforming to a well established standard shape and size of angioplasty guidewires.

(h) Having an ability to be held in a central lumen of angioplasty catheter and held there to be activated at any time during angioplasty procedure.

(i) Having the transducer located forward of the angioplasty balloon thus, in an angioplasty of narrow occlusions, having an ability to scan through occluded areas in front of the catheter and then following it with an angioplasty balloon.

Further objects and advantages of the present invention will become apparent from a study of the drawing figures described in next chapter.

DRAWING FIGURES

In the drawings, similarly related parts have the same number, but a different alphabetic suffix.

REFERENCE NUMERALS IN DRAWING FIGURES

Imaging wire of the present invention may consist of:

| | |
|---|---|
| 10 | catheter guide |
| 11 | transducer seat |
| 12 | distal guidewire |
| 13 | manipulating bend |
| 14 | ultrasonic transducer |
| 15 | outside metallization of transducer |
| 16 | internal insulation coat |
| 17 | transducer metallization |
| 18 | metal core of wire |
| 19 | main insulation |
| 20 | outside metallization shield |
| 21 | external protective coat |
| 22 | encoder element |
| 23 | protective ball |
| 24 | proximal end of catheter guide |
| 25 | electrical wires |
| 26 | encoder disk |
| 27 | external protective coat |
| 28 | rotary drive unit |
| 29 | electric motor |
| 30 | electronic computer |
| 31 | angioplasty catheter |
| 32 | exposed shield |
| 33 | rotating mandrel |
| 34 | rotary bearing |
| 35 | cable |
| 36 | housing |
| 37 | slip contacts |
| 38 | rotor winding |
| 39 | stator magnet |
| 40 | switch assembly |
| 41 | return spring |
| 42 | switch contacts |
| 43 | switch cover |
| 44 | inflatable balloon |
| 45 | insulating part |
| 46 | metal contact |
| 47 | mandrel opening |
| 48 | encoder housing |
| 49 | push button |

Description—FIGS 1 through 5

Figure 1:
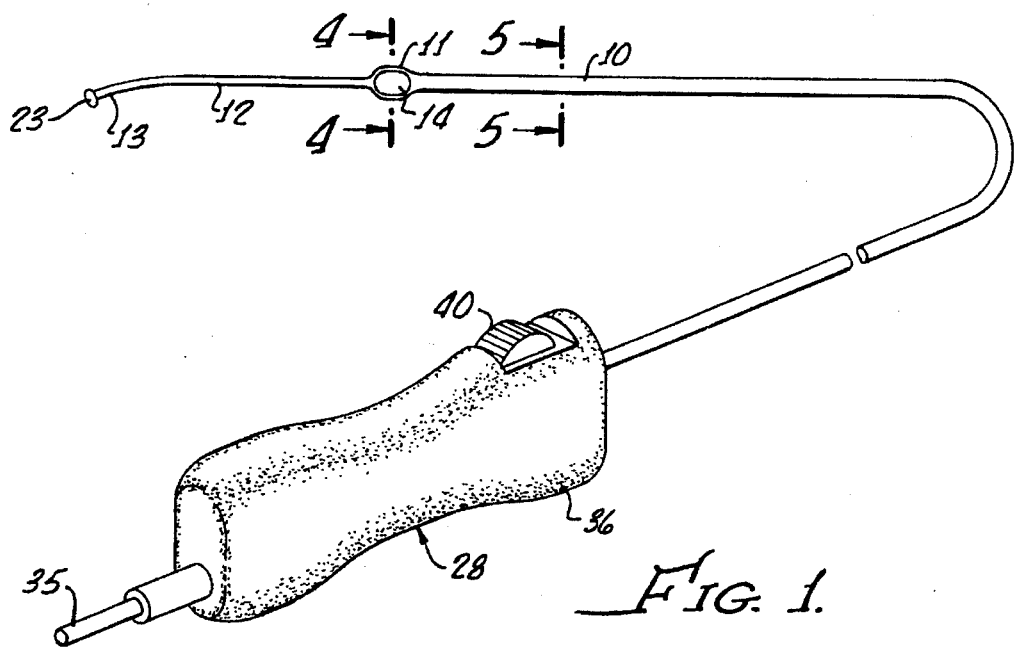
FIG. 1 Shows an overall view of a typical embodiment of the present invention.

FIG. 1 Shows an overall view of a typical embodiment of the present invention. Catheter guide 10 part of imaging guidewire is a long stainless steel wire having been coated with multiple layers of insulation and metal, having an outside diameter of approximately 0.018" in diameter, suitable for insertion into the central lumen of an angioplasty catheter. Guide 10 is approximately 39.3 to 78.74 inches (1000 to 2000 mm) long.

Catheter guide 10, at its distal end, is connected with a transducer seat 11, which is flattened and generally wider than the metal core of the rest of imaging wire. Transducer seat 11 may be made of the same metal as guide 10, such as stainless steel 303. Guide 10, transducer seat 11 and distal guidewire may be made of the same piece of metal ground to a desired shape.

Transducer seat 11 is elliptically shaped, 0.050"×0.030" large and approximately 0.015" thick (1.52×0.76×0.38 mm).

An ultrasonic transducer 14 is attached to transducer seat 11 with a thin film of electrically conductive epoxy, or other suitable, electrically conductive adhesive.

Ultrasonic transducer 14 is made of a thin, approximately 0.005 inches (0.123 mm) thick disk, of approximately 0.030 inches (0.76 mm) in diameter PZT (lead zirconate-titanate) material such as type EC-66, manufactured by EDO Corporation, Salt Lake City, Utah.

Distal guidewire 12 is connected with seat 11 and is made of stainless steel approx 0.006" (0.152 mm) in diameter. At the distal end of distal guidewire 12 a manipulating bend 13 may be formed, for easier access to vessel tributaries. Additionally a small protective ball 23 may be formed at the distal end of distal guidewire 13. Protective ball 23 is approximately 0.009 of an inch (0.23 mm) in diameter.

Distal guidewire 12 and ball 23 are coated with a thin (approximately 3–6 micrometers thick) layer of teflon or other suitable, insulating plastic material having a low coefficient of friction.

Catheter guide 10 at a proximal end 21 is connected with a rotary drive unit 28. Drive unit 28 consists of a housing 36 to which a switch assembly 40 and cable 35 are attached. Detailed description of drive unit 28 is provided in connection with FIG. 6.

Figure 2:
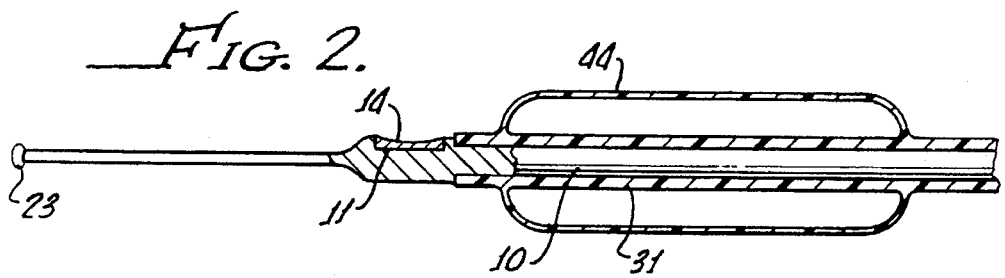
FIG. 2 Shows an axial cross section through a typical imaging guidewire of the present invention, inserted into a lumen of an angioplasty catheter, in the plane perpendicular to the surface of an ultrasonic transducer.

FIG. 2. Shows an axial cross section through a typical imaging guidewire of the present invention, (See line 2A—2A of FIG. 3) inserted into a lumen of an angioplasty catheter, in the plane perpendicular to the surface of an ultrasonic transducer.

Catheter guide 10 is fitted into a central lumen of angioplasty catheter 31.

Transducer seat 11 and transducer 14 are projecting outside angioplasty catheter 31, and are in position for a rotating scan. An inflatable balloon 44 of angioplasty catheter 31 may be inflated with a slight pressure to center the imaging guidewire in the lumen of a blood vessel. Balloon 44 may be inflated with an extensive pressure if angioplasty of vessel walls is desired.

Figure 2A:
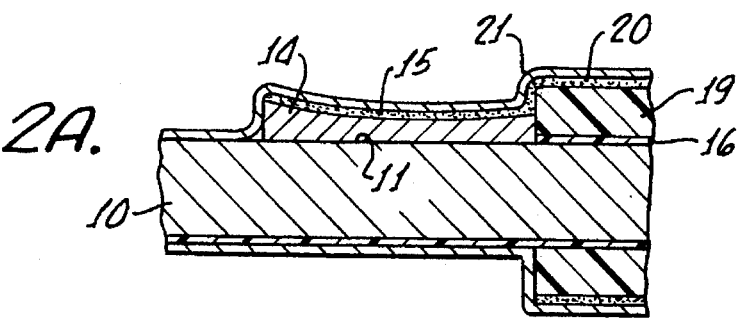
FIG. 2A shows a detailed axial cross sectional view of the transducer taken along the line 2A—2A of FIG. 3.

FIG. 2A shows a detailed cross sectional view of the transducer 14 of FIG. 2 taken axially, through transducer 14 and transducer seat 11, as well as through metal a metal core 18. Transducer 14 is attached to transducer seat 11 with a film of conductive epoxy or other suitable, conductive adhesive.

Metal core 18, made most suitably of stainless steel (such as type 303), has been coated with a thin (3 micrometers thick) layer of polyethylene, constituting an internal insulation coat 16. Internal insulation coat 16 has been locally removed to permit attachment and electrical contact of transducer 14 with metal core 18.

A main insulation 19 has been applied over the length of catheter guide 10. The thickness of insulation 19 is approximately 120 micrometers or 0.0048 inches. Insulation 19 may be made of homogenous material such as teflon or polyethylene, or if stiffer catheter guide is required it may be made of polyester resin, reinforced with thin glass or carbon fibers, wound spirally over metal core 18.

Outside metallization shield 20 is a thin layer of aluminum, nickel, sliver or other metal, approximately 10 to 20 micrometers thick, deposited over insulation 19. Shield 20 may be deposited using vacuum deposition process.

An outside metallization 15 of transducer connects the upper surface of transducer 14 with outside metallization shield 20 or may be a part of metallization 20.

An external protective coat 21 has been applied over metallization 20. Coat 21 may consist of teflon 3–5 microns thick, vacuum deposited over metallization 20.

Figure 3:
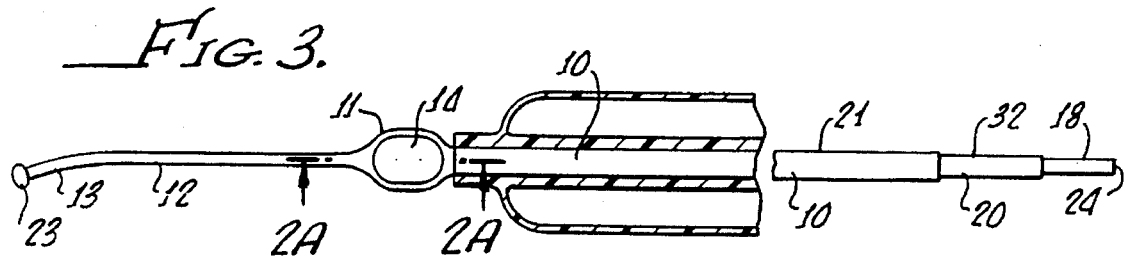
FIG. 3 Shows a partial axial cross section through a typical imaging guidewire of the present invention, inserted into a lumen of an angioplasty catheter, in the plane parallel to the surface of an ultrasonic transducer.

FIG. 3 Shows a partial axial cross section through a typical imaging guidewire of the present invention, inserted into a lumen of an angioplasty catheter, in the plane parallel to surface of an ultrasonic transducer.

Transducer seat 11 is centered with angioplasty catheter 31 as a result of guide 10 having been inserted into the central lumen of angioplasty catheter 31.

Distal guide wire 12, projecting outside transducer seat 11, may have manipulating bend 13 for easier entry into branches of the blood vessels.

Protective ball 23 may be attached at a distal end of distal guidewire 12.

Near a proximal end 24 of catheter guide 10, external protective coat 21 has been removed, forming an exposed shield 32, which is connected, or may be a part of metallization shield 20.

A part of catheter guide 10, closest to proximal end 24, has its entire coating removed, exposing metal core 18.

Metal core 18 and the exposed shield allow for a convenient electrical connection to transducer 14 from rotary drive unit 28.

Figure 4:
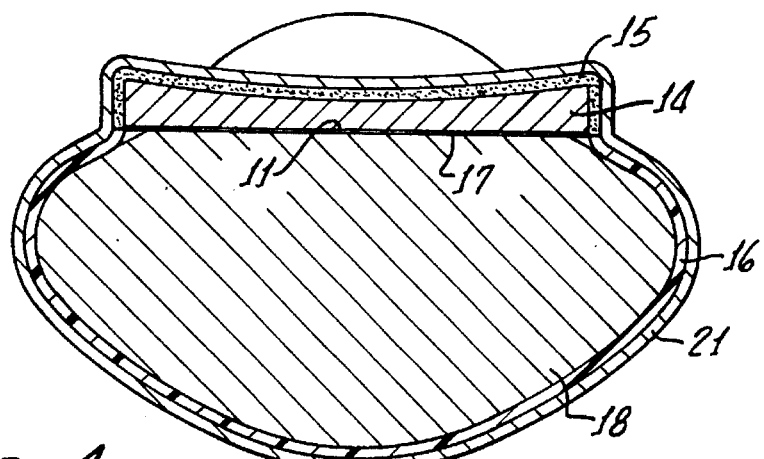
FIG. 4 Shows a cross sectional view, taken along line 4—4 of FIG. 1 of a typical imaging guidewire of the present invention, through ultrasonic transducer, in the plane perpendicular to the axis of an imaging guidewire.
Figure 5:
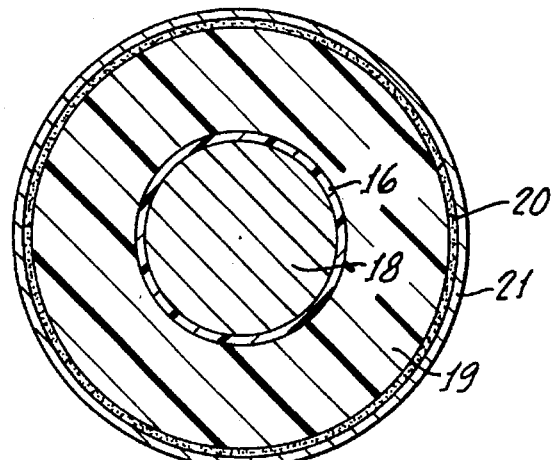
FIG. 5 Shows a cross sectional view of a typical imaging guidewire of the present invention, proximally from an ultrasonic transducer, in the plane perpendicular to the axis of an imaging guidewire.

FIG. 4 Shows a cross sectional view, takes along line 4—4 of FIG. 1, of a typical imaging guidewire of the present invention, through an ultrasonic transducer, in a plane perpendicular to the axis of the imaging guidewire and FIG. 5 shows a cross sectional view taken along line 5—5 of FIG. 1.

Metal core 18 is larger in this location (having a longer dimension of approximately 0.030 inches or 0.76 mm), slightly elliptical in shape, flattened on top forming transducer seat 11.

Internal insulation coat 16 has been removed in the area of transducer seat 11, to allow electrical contact between core 18 and transducer 14.

Transducer 14 is made of a thin disk of PZT, metallized on its two largest surfaces with a transducer metallization 17, which may be in a form of a vacuum deposited gold layer, approximately 1–3 micrometers in thickness.

Transducer 14 is attached to transducer seat 11 through a thin film of electrically conductive epoxy such as Tra-Duct 2924 manufactured by Tra-Con, Inc. Medford, Mass. Electrical contact is thus maintained between transducer metallization 17 at the bottom surface of transducer 14 and metal core 18 and electrical signals may be supplied to bottom surface of transducer 14 through metal core 18.

Transducer 14 is metallized on its upper surface with outside metallization 15 of the transducer, which is connected with outside metallization shield 20. Metallization coats 15 and 20 may be done in one operation.

Connection between metallization coats 15 and 20 allows for an electrical signal to be supplied to upper surface of transducer 14 through metallization shield 20.

A protective coat 21 is applied over the entire surface of the imaging guidewire to protect it from chemical reactions with body fluids and tissue and to minimize friction on the surface of the imaging guidewire. Protective coat 21 is most suitably made by vacuum deposition of teflon.

FIG. 5 Shows a cross section of a typical imaging guidewire of the present invention, proximally from an ultrasonic transducer, in a plane perpendicular to the axis of the imaging guidewire.

Metal core 18 is circular and approximately 0.0066 inches (0.164 mm) in diameter. Metal core 18 has been coated with a thin layer of internal insulation coat 16.

Insulation 19 has been deposited over coat 16. The thickness of insulation 19 is approximately 120 micrometers or 0.0048 inches.

Insulation 19 may be made of homogenous material such as teflon or polyethylene, or if stiffer catheter guide is required it may be made of polyester resin, reinforced with thin glass or carbon fibers, wound spirally over metal core 18.

Outside metallization shield 20 is a thin layer of aluminum, nickel, silver or other metal, approximately 10 to 20 micrometers thick, deposited over insulation 19. Shield 20 may be deposited using a vacuum deposition process.

Metallization shield 20 is connected with transducer metallization coat 15, and provides an electrical connection to the outside surface of transducer 14 and electrical shielding for the signals transmitted over metal core 18.

Protective coat 21 is applied over the entire surface of the imaging guidewire.

Figure 6:
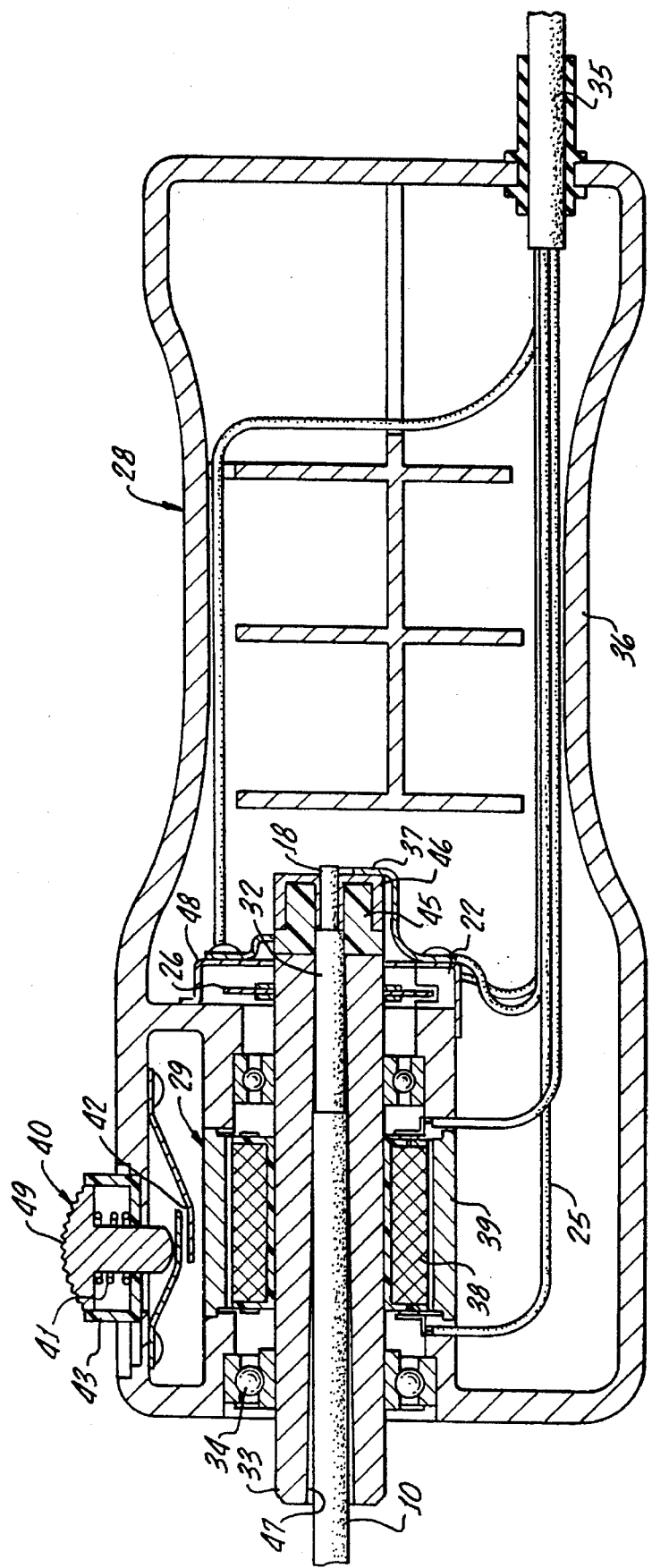
FIG. 6 Shows an axial cross section through a typical rotary drive unit for the imaging guidewire, taken along line 5—5 of FIG. 1 of the present invention.

FIG. 6 Shows an axial cross section through a typical rotary drive unit for imaging guidewire of the present invention.

Rotary drive unit 28 consists of a plastic housing 36, shaped in the form of a compact handle.

A rotating mandrel 33 is rotatably attached in bearings 34, permitting for rotation of mandrel 33. Mandrel 33 is approximately 4 inches (101 mm) long and 0.625 inches (15.8 mm) in diameter. Mandrel 33 has a cylindrical mandrel opening 47, whose dimension resembles the diameter of catheter guide 10. Mandrel opening 47 may be slightly tapered, to allow for locking of catheter guide 10 inside mandrel opening 47.

Mandrel 33 may be made of stainless steel such as the 17-4 type. Electrical connection between exposed shield 32 and stationary slip contacts 37 takes place through mandrel 33.

At its internal end mandrel 33 has an insulating part 45, over which a metal contact 46 has been made. Contact 46 may be made by molding a cylindrical metal part into insulating part 45. The purpose of metal contact 46 is transmission of signals from exposed metal core 18 at the distal end of the catheter guide to slip contacts 37.

Encoder disk 26 is attached to mandrel 33 and has an ability to rotate with mandrel 33. Disk 26 contains marks indicating angular position of mandrel 33. Marks on encoder disk 26 can be read by an optical encoder element 22, which signals to electronic computer 30 angular position of mandrel 33.

Encoder disk 26 and element 22 may be covered by an encoder cover 48 to protect them from contamination.

An electric motor 29 is built into housing 36. Motor 29 consists of rotor windings 38, wound on the rotating mandrel 33 and stator magnet 39, surrounding rotor windings 38.

A switch assembly 40 mounted in the upper area of housing 36 consists of push button 49, retained away from housing 36 by a return spring 41 and a switch cover 43, which is made of flexible plastic material.

Push button 49 may be pressed inside housing 36 or locked in the pushed position by sliding it along the axis of housing 36.

A pair of switch contacts 42 may be closed when pressure of push button 49 deflects one of switch contacts 42 to engage with second one of contacts 42.

Electrical signals to and from slip contact 37, encoder element 22, and electrical power to drive rotor windings 38 through switch contacts 42 is delivered via a set of electrical wires 25.

Electrical wires 25 are routed in a common cable 35 to electronic computer 30 (not shown).

Method of manufacturing of imaging guidewire

The imaging guidewire may be manufactured using the following procedure:

The metal core 18 is shaped by grinding. Shaping operation may include shaping catheter guide 10 part, transducer seat 11, distal guidewire 12, protective ball 23.

Next a manipulating bend 12 may be formed.

Guidewire is then subjected to stress relieving which involves heating to and holding at elevated temperatures and controllably cooling. Such treatment is conventionally done to relieve machining stresses in the part.

Next internal insulation coat 16, consisting of a thin coat of polyethylene or parylene (such as parylene C) of approximately 3 micrometers is deposited over the entire surface of imaging guidewire in a vacuum deposition process.

Next coat 16 is locally removed from an area of transducer seat 11 by grinding.

Next transducer 14 is attached to transducer seat 11 via bonding with electrically conductive adhesive.

Transducer 14 may have been previously coated on both larger surfaces with transducer metallization 17, consisting of thinly (approximately 1 micrometer) deposited gold or silver.

The metal is deposited in such a way that the edges and cylindrical surfaces of transducer 14 are free from conductors to prevent a short circuit.

A thick coat of main insulation 19 is applied on the length of catheter guide 10. This may be done in a process of filament winding. In such a process a thin fiber of glass or carbon or other reinforcing material is wetted with polyester resin and spirally wound on core 18 in two directions while strung between two rotating chucks.

The bending stiffness of the catheter guide may be controlled by varying the pitch of spiral windings of the reinforcing fibers. The fiber is wound back and forth creating a crossing pattern.

Another method, if higher stiffness of the catheter guide is not desired, is to thickly coat catheter guide with approximately 120 micrometers of polyethylene or other suitable plastic, electrical insulator material to form main insulation 19 in a conventional coating process.

Next coats of outside metallization of transducer 15 and outside metallization shield 20 are applied. Both layers of metallization may be applied in the same vacuum deposition process. Distal guidewire 12 may be masked off from this operation.

Next a thin layer of teflon is applied on the entire surface of the imaging guidewire to create external protective coat 21. The thickness of this coat may be between 1 and 5 micrometers Operation In a typical procedure the physician performing the catheterization procedure using the imaging guidewire inserts the guidewire into the blood vessel via an introduction sheath. The guidewire at this point may be already routed through an angioplasty catheter.

Once the guidewire is advanced into the area of a vessel suspected of being diseased, the physician may connect the proximal end of the catheter guide of the imaging guidewire to rotary drive unit 28, by inserting it into mandrel opening 47, and may activate rotary drive unit 28 by pressing push button 49.

Upon pressing of button 49 mandrel 33 is rotated by electric motor 29. Since the proximal end of the catheter guide 24 part of the imaging guidewire is inserted into mandrel 33, the entire guidewire is rotated with the speed of rotation conforming to the speed of rotation of mandrel 33.

The angle of rotation of the imaging guidewire is read electronically by encoder element 22 from encoder disk 26 rotating together with mandrel 33.

Electrical signals from encoder element 22 are transmitted to electronic computer 30 through electrical wires 25 and cable 35.

Electrical pulse signals to activate transducer 14 as well as signals received from transducer 14 are transmitted along the length of the imaging guidewire through metal core 18 and outside metallization shield 20, a set of slip contacts 37, electrical wires 25 and cable 35 to and from electronic computer 30.

Transducer 14 operates on principle of piezoelectricity. When an electric signal is applied across the width of transducer 14, thanks to piezoelectric properties of PZT material, a change occurs in physical dimension of the PZT transducer, which leads to creation an acoustic wave in the medium surrounding transducer 14.

Summary, Ramification, and Scope

Accordingly, the reader will see that the ultrasound imaging guidewire of the present invention presents a novel construction and expanded capabilities and offers novel applications of intravascular ultrasound imaging.

Previous inventions and articles have not cited nor anticipated a similar ultrasound imaging guidewire.

The imaging guidewire permits substantial benefits over the existing or anticipated catheters for intraluminal, ultrasound imaging. Imaging guidewire of the present invention permits a physician to monitor plaque in front of the distal tip of angioplasty catheter and thus helps the physician make decision whether to perform angioplasty and gives information about the vessel wall.

Similarly the imaging guidewire of the present invention helps reduce trauma of catheterization by avoiding multiple insertions of catheters, by permitting ultrasound imaging without necessity to insert an imaging catheter.

Furthermore, the present invention has additional advantages in that:

it allows for a simple construction of an imaging guidewire, it allows for an inexpensive method of manufacturing of imaging guidewire and simple attachment of the transducer, a small diameter of imaging guidewire and transducer allows for insertion into narrow, and coronary blood vessels, construction of imaging guidewire permits its insertion into guidewire lumen of angioplasty catheters, While the above description contains many specificities, the reader should not construe these as limitation on the scope of the invention, but merely as exemplifications on the typical embodiments thereof.

Those skilled in the art will envision many other possible variations are within its scope. For example skilled artisans will readily be able to change the dimensions and shapes of the various embodiments. They will also be able to make many variations on the shape of the transducer assembly, and the method of its attachment to a transducer seat.

They can also vary the materials used for parts of imaging guidewire, such as other metals and plastic or plastic composites and employ different manufacturing techniques for their fabrication.

Similarly they can vary the material used for ultrasonic transducer such as PVDF (polyvinylidiene fluoride), PZT, BaTiO3 (barium titanate), lead metaniobate.

Also the shape of distal guidewire, transducer seat and catheter guide may be changed.

Accordingly the reader is requested to determine the scope of the invention by the appended claims and their legal equivalents, and not by the examples which have been given.

We claim:

1. Imaging/angioplasty apparatus for use in a human or animal vessel, the apparatus comprising:

an angioplasty catheter having a guidewire lumen surrounded by inflatable balloon means for both centering of the angioplasty catheter within a vessel and performing angioplasty of vessel walls;

a flexible elongate member sized for insertion through said guidewire lumen and having a transducer seat portion disposed between said angioplasty catheter and a distal end of said flexible elongate member, with no housing between said transducer seat portion and said vessel walls, said flexible elongate member being rotatable within said guidewire lumen and centerable within the vessel by inflation of the balloon means;

ultrasonic transducer means, fixed to said seat portion for rotation therewith, for imaging plaque within the vessel in front of the angioplasty catheter.

2. The apparatus according to claim 1 wherein said seat portion has an elliptical shape.

3. The apparatus according to claim 2 further comprising means for rotation of said flexible elongate member and transducer within the vessel and guidewire lumen, said means for rotation being disposed at a proximal end of said flexible elongate member.

4. The apparatus according to claim 3 wherein said flexible elongate member comprises a metal core and said seat portion comprises a flattened portion of said metal core.

5. The apparatus according to claim 4 further comprises electrical conductor means, disposed over said metal core, for conducting electrical signals to and from said transducer, and an electrical insulation material disposed between said electrical conductor means and said metal core.

6. The apparatus according to claim 5 wherein said electrical insulation material comprises a plurality of plastic fibers spirally wound around the metal core.

7. The apparatus according to claim 1 wherein the angioplasty catheter has an outside diameter of less or about 0.02 inches.

8. The apparatus according to claim 7 wherein the seat portion has dimensions of about 0.05 inches by 0.03 inches with a thickness of about 0.015 inches.

9. Imaging apparatus for use in a human or animal vessel, the apparatus comprising:

a flexible elongate member sized for insertion into a vessel and having a transducer seat thereon proximate a distal end of said flexible elongate member;

ultrasonic transducer means, fixed to said transducer seat for imaging plaque within the vessel;

means for rotating the flexible elongate member and ultrasonic transducer within the vessel; and balloon means for stabilizing and centering the transducer seat and transducer during rotation thereof, said balloon means being disposed around a guidewire lumen, said elongate member being disposed through said guidewire lumen, with said transducer seat disposed between said balloon means and said distal end with no housing between said transducer seat and the vessel.

10. The apparatus according to claim 9 wherein said transducer seat has an elliptical shape.

11. The apparatus according to claim 10, wherein said flexible elongate member comprises a metal core and said transducer seat comprises a flattened portion of said metal core.

12. The apparatus according to claim 11, further comprises electrical conductor means, disposed over said metal core, for conducting electrical signals to and from said transducer, and an electrical insulator material disposed between said electrical conducting means and said metal core.

13. An angioplasty method comprising the steps of:
(a) inserting an elongate member, with an ultrasonic transducer, disposed thereon, through a guidewire lumen in an angioplasty catheter;
(b) inserting the ultrasonic transducer and angioplasty catheter into a vessel with the transducer preceding the catheter enabling direct exposure of said ultrasonic transducer to vessel walls;
(c) imaging the vessel walls with the inserted transducer at a selected position within the vessel;
(d) after imaging, moving the angioplasty catheter to the selected position; and
(e) performing angioplasty on the imaged walls by inflating a balloon surrounding the guidewire lumen.

14. The method according to claim 13 further comprising the step of repeating steps (c), (d) and (e).

15. The method according to claim 13 further comprising the step of centering the transducer within the vessel during imaging by inflating the balloon.

16. The method according to claim 15, further comprising the step of rotating the transducer during imaging of the walls.

17. The method according to claim 16, wherein the step of imaging walls comprises generating an ultrasonic signal by supplying an electrical signal to the ultrasonic transducer, receiving electrical signals from the ultrasonic transducer and converting the received electrical signal to a video image.

18. A method for use in imaging an interim wall of a vessel, said method comprising:
(a) inserting an ultrasonic, transducer, disposed on an elongate member, into a vessel;
(b) centering the transducer within the vessel by inflating a balloon surrounding the elongate member, said transducer being spaced apart from vessel walls by the centering and enabled for direct exposure to said vessel walls;
(c) rotating the centered transducer within the vessel; p1
(d) generating an ultrasonic signal by supplying an electrical signal to the transducer; and
(e) receiving ultrasonic signals with the transducer.

19. The method according to claim 18, further comprising the step of converting electrical signals, corresponding to the received ultrasonic signals, into a video image.

20. The method according to claim 18, further comprising the steps of deflating the balloon, moving the inserted ultrasonic-transducer to another position within the vessel and thereafter repeating steps (b), (c), (d) and (e).

* * * * *